United States Patent

Temple

[11] Patent Number: 5,961,963
[45] Date of Patent: Oct. 5, 1999

[54] ANTIPERSPIRANT COMPOSITION

[75] Inventor: John Temple, Bebington, United Kingdom

[73] Assignee: Helene Curtis, Inc., Chicago, Ill.

[21] Appl. No.: 09/024,813

[22] Filed: Feb. 17, 1998

[30] Foreign Application Priority Data

Feb. 17, 1997 [GB] United Kingdom .................. 9703261

[51] Int. Cl.$^6$ ............................... A61K 7/32; A61K 7/00
[52] U.S. Cl. ................................. 424/65; 424/66; 424/67; 424/68; 424/400; 424/401
[58] Field of Search .................................. 424/65, 66, 67, 424/68, 400, 401

[56] References Cited

U.S. PATENT DOCUMENTS

| | | | |
|---|---|---|---|
| 4,152,416 | 5/1979 | Spitzer et al. | 424/46 |
| 4,695,451 | 9/1987 | Straw et al. | 424/47 |
| 4,806,338 | 2/1989 | Smith | 424/47 |
| 5,814,309 | 9/1998 | Panitch | 424/651 |

FOREIGN PATENT DOCUMENTS

| | | |
|---|---|---|
| 0343843 | 9/1993 | European Pat. Off. . |
| 94/22420 | 10/1994 | WIPO . |

OTHER PUBLICATIONS

International Search Report No. PCT EP 98/00812—dated Jun. 24, 1998.

Derwent Abstract AN 94/290,808—XP002069146 "Antibacterial deodorizing and cooling spray agent for feet e.g., easing tiredness—comprises cooling agent contg. Pentane liq. Petroleum gas, ethanol, deodorizing agent, menthol and titanium oxide microcapsules" Aug. 9, 1994.

Derwent Abstract No. 239361—XP002069143—"Aerosol antiperspirants containing metal salts powders and isopentane and/or pentane" May 20, 1991.

Derwent Abstract No. 75105—XP 002069144—"Antiperspirant and insect repellent aerosols" Oct. 28, 1985.

Derwent Abstract No. 119859—XP 002069145 Apr. 19, 1991.

*Primary Examiner*—Shelley A. Dodson
*Attorney, Agent, or Firm*—Matthew Boxer

[57] ABSTRACT

An aerosol antiperspirant composition for topical application to the human skin, comprising an antiperspirant active and a propellant, characterised in that the propellant comprises pentane.

8 Claims, No Drawings

ANTIPERSPIRANT COMPOSITION

The present invention relates to antiperspirant compositions. More particularly, the invention relates to aerosol compositions having improved cosmetic characteristics.

Antiperspirant and deodorant compositions can be applied to the skin by a variety of methods. Generally, such compositions comprise a carrier vehicle material in addition to an antiperspirant and/or deodorant active, the carrier and active being selected in accordance with factors such as the method of application, the intended use, the desired rheology and the desired cosmetic characteristics.

Aerosol compositions have gained wide consumer acceptance. Aerosol antiperspirant compositions generally comprise an anhydrous system comprising an antiperspirant salt dispersed in a liquid vehicle together with a liquefied volatile propellant in a pressurised aerosol container.

Consumers can be generally divided into two classes—those who favour the use of antiperspirant aerosol compositions and those who favour deodorant aerosol compositions. The presence of the antiperspirant active in antiperspirant aerosol compositions imparts different cosmetic or sensory properties to the antiperspirant aerosol compositions which are absent from alcoholic deodorant formulations.

Generally, deodorant composition contain high levels (usually 30% or over) of short-chain monohydric alcohol, which has a deodorising effect and which imparts a cold or fresh feeling to the skin.

Conversely, antiperspirant compositions are usually incompatible with high levels of alcohol and/or water, due to the tendency to form corrosive solutions, and therefore generally tend to comprise a relatively high proportion of compounds such as volatile cyclic silicones in their cosmetic vehicles, which have a low heat of evaporation compared to ethanol and water. As such, antiperspirant compositions tend to produce less of a cooling sensation on application, and generally do not impart such a fresh feeling.

Many consumers, therefore, choose deodorants over antiperspirants in order to achieve a cold or fresh feeling on application. However, deodorants unlike antiperspirants fail to prevent sweat generation and also exhibit poor malodour reduction over time.

Accordingly, consumers who select an aerosol deodorant over an antiperspirant for initial freshness fail to enjoy the additional benefits of an antiperspirant.

U.S. Pat. No. 4,152,416 describes aerosol antiperspirant compositions capable of dispensing an astringent solid with low mistiness and dustiness. A polymer gum is used in the aerosol composition to reduce the mistiness and/or dustiness of the aerosol composition.

U.S. Pat. No. 4,806,338 also describes the use of amino functional silicones in antiperspirant aerosol compositions in order to improve the cosmetic properties of the composition. Moreover, U.S. Pat. No. 4,806,338 implies that the use of such silicones helps to prevent undesirable cooling on the skin.

EP 343,843 of the Mennen Company also describes the use of a substantivity fluid made up of a silicone polymer dissolved in a carrier fluid to prevent clogging of aerosol valves at low delivery rates.

Co-pending application GB 96124477.1, in the name of the applicants, describes an aerosol antiperspirant composition in which polymers are incorporated in the composition for the purpose of retarding evaporation of propellant gases in the composition, and thereby causing a proportion of the propellant gas to be retained with the composition, and deposited on the skin. The evaporation of this propellant gas on the skin generates a cooling sensation, and thereby provides the composition with this sensory benefit.

According to the invention there is provided an aerosol antiperspirant composition for topical application to the human skin, comprising an antiperspirant active and a propellant, characterised in that the propellant comprises pentane.

Compositions according to the invention typically produce a cool feeling on application.

In highly preferred aspects of the invention, the propellant composition comprises from 1–50% part pentane gas, which can be n-pentane, isopentane or cyclopentane; preferably the propellant comprises 2–40%, more preferably 5–25% pentane. Of the possible pentane species, n-pentane is preferred. Preferably the pentane level is less than 40%, since at levels above this the pentane in the dispensing container causes the vapour pressure to be depressed too much, and the aerosol container may block due to insufficient vapour pressure in the container.

The compositions according to the invention may additionally comprise a polymer, and the propellant is conveyed and deposited on the skin by a propellant-polymer mix. Preferably, the polymer comprises a silicone polymer. The silicone polymer can be a silicone gum or a silicone fluid. However, an advantage of compositions according to the invention is that sensory benefits can be obtained over compositions which contain only other ordinary propellants, such as isobutane, propane, butane, or mixtures thereof, also without the use of additional polymers to induce cooling.

In an alternative embodiment, the invention relates to the use of pentane as a skin cooling agent in the preparation of an aerosol composition, which may also comprise an antiperspirant active.

If the composition does comprise an additional polymer to enhance the cooling sensation on application, conveniently the polymer is a polydimethylsiloxane gum, preferably a dimethicone and/or dimethiconol gum.

Accordingly, the present invention provides an antiperspirant composition having the skin cooling benefits of an alcoholic deodorant composition, in a composition which is totally free, or substantially free (i.e. containing less than 1% by weight) of short chain monohydric alcohols such as ethanol or isopropanol, but is also substantially free (i.e. contains less than about 4%) of water.

Accordingly, a consumer can enjoy the sensory benefits of a traditional alcoholic aerosol deodorant composition, while enjoying the deodorant and antiperspirant efficacy of a traditional aerosol antiperspirant composition.

The antiperspirant material of the invention is preferably a particulate antiperspirant, and can be any of the known antiperspirant active materials. Particularly preferred materials are astringent metallic salts, in particular the inorganic and organic salts of aluminium, zirconium and zinc and mixtures thereof. Particularly preferred are the aluminium and zirconium salts such as aluminium halides, aluminium hydroxide halides, zirconium hydroxy halides, zirconium oxide halides and mixtures thereof. Generally, such antiperspirant salts for example comprising aluminium and/or zirconium salts are any of those well known in the art. U.S. Pat. No. 4,152,416 describes various aluminium zirconium salts which are suitable for use in the present invention. Typically, the antiperspirant active is present at a level of from about 0.1% to about 20% by weight of the composition.

Generally, when they are used, the silicone gums suitable for use in the present invention are as defined in U.S. Pat.

No. 4,152,416 and have a viscosity ranging from about 0.5 to 100 $m^2sec^{-1}$ (500,000 to 100,000,000 centistokes) at 25° C. Typical silicone gums are the polydimethylsiloxane polymers such as dimethiconol and dimethicone gums.

The silicone gum if used is preferably present at levels from about 0.01% to about 6% by weight, more preferably from about 0.02% to about 4% by weight of the composition.

Alternatively or in addition to the silicone gum, silicone fluids can also be used to generate an enhanced cooling effect in compositions according to the invention. Suitable fluids are the DC200 series of silicones available from Dow Corning.

The aerosol antiperspirant compositions of the present invention also preferably contain additional solvent or carrier material. Particularly preferred are volatile low viscosity silicones.

The term "volatile" also includes materials that are only slowly volatile and require a longer time to evaporate than e.g. volatile silicones.

A particularly preferred series of volatile liquid carriers are the cyclomethicone liquids. Generally, the volatile low viscosity liquids usable in the present invention have a boiling point of at least 100° C. and a viscosity of less than $1\times10^{-5}$ $m^2sec^{-1}$ (10 centistokes) at 25° C. The volatile silicone fluids are utilised at levels of about 1% to about 30%, preferably from about 2.5% to about 14.5% by weight of the composition.

Suitable silicone gums and volatile silicone fluids are available as standard proprietary material mixes or solutions e.g. Q2-1401 available from Dow Corning. SE30, a silicone gum available from the General Electric Company can also be used.

The compositions of the invention also contain one or more volatile aerosol propellant materials which in a gaseous state carry the other components of the invention in particulate or droplet form, in addition to pentane. Suitable propellants have a boiling point in the range of from −45° C. to about 5° C. and are present at levels from about 20% to 90% by weight of the composition.

For the further propellant, suitable other aerosol propellants are well known in the art and include the chemically inert hydrocarbons such as propane, n-butane, isobutane, cyclopropane, dimethyl ether and mixtures thereof.

The antiperspirant compositions of the present invention may also comprise a suspending agent to suspend the antiperspirant actives. Suitable suspending agents include colloidal silicas and hydrophobic clays such as the bentonites and hectorites. A particularly preferred bentonite is hydrophobic bentonite e.g. Bentone, which is commercially available and is a bentonite treated with hydrophobic cationic materials. Typically the suspending agents are utilised at a level of from about 0.3% to 3% by weight of the composition.

In addition, masking agents to conceal antiperspirant active residue suitable for use in the compositions according to the present invention can be included. Suitable masking agents may be selected from aliphatic hydrocarbons (e.g. C8–C30, preferably C10–C16, more preferable C12–C15 linear or branched hydrocarbons), aliphatic esters, aromatic esters and mixtures thereof. The preferred residue masking agents for use in the compositions according to the present invention are C8–C30, preferably C10–C16, more preferably C12–C15 mono- and di-alkyl esters of aromatic carboxylic acids inclusive of the benzoates and phthalates. Suitable masking agents include isopropyl myristate, isopropyl palmitate, polydecenes, Fluid AP, the Finsolv range of benzoate esters and mixtures thereof which can be used at ranges from 0.5% to 25% by weight of the composition.

In addition to the above mentioned ingredients customary adjuncts of aerosol antiperspirant compositions can also be included in the composition. Such adjuncts include perfumes, bactericides, fungicides, emollients and other skin treating materials.

The following are examples of compositions within the scope of the present invention. In the examples, all percentages of the specified ingredients are weight percentages.

EXAMPLE 1

| Material | Chemical | Level (% wt/wt) |
| --- | --- | --- |
| Antiperspirant active | Activated aluminium chlorohydrate | 5.0 |
| Volatile silicone (DC 245) | Cyclomethicone | 6.3 |
| Masking agent (Fluid AP) | PPG-14 butyl ether | 2.0 |
| Fragrance | | 0.7 |
| Suspending agent (Bentone 38) | Quaternium-18 hectorite | 1.0 |
| Propellant | n-pentane | 10.0 |
| Propellant | Butane/Isobutane/Propane | 75.0 |

| Component | % (w/w) |
| --- | --- |

EXAMPLE 2

| Antiperspirant active (Aluminium chlorohydrate) | 10.0 |
| --- | --- |
| Volatile silicone (Cyclomethicone) | 3.1 |
| Masking agent (Finsolv TN) | 5.0 |
| Suspending agent (Bentone 38) | 1.0 |
| Fragrance | 0.7 |
| Silicone gum (Q2-1401) | 0.2 |
| Propellant (n-pentane) | 10.0 |
| Propellant (Butane/Isobutane/Propane) | 70.0 |

EXAMPLE 3

| Antiperspirant active (Activated aluminium chlorohydrate) | 4.0 |
| --- | --- |
| Volatile silicone (Cyclomethicone) | 3.8 |
| Suspending agent (Bentone 38) | 1.0 |
| Fragrance | 1.0 |
| Silicone gum (Q2-1401) | 0.2 |
| Propellant (n-Pentane) | 20.0 |
| Propellant (Butane/Isobutane/Propane) | 70.0 |

Experimental

Temperature measurements were conducted during the spraying of various aerosol compositions. In particular, an instrument comprising three K-type thermocouples arranged in a vertical line was used to measure the temperatures of various sprays. The temperature profile of different compositions of sprays was measured when sprayed at the thermocouple array for a period of 2 seconds, from a distance of 10 cm.

The compositions of Examples 2 and 3 above were sprayed, as were a nominal alcoholic deodorant composition (comprising 50% propane propellant, 0.5% perfume and 49.5% ethanol), and a formulation generally similar to Example 3 above (i.e. containing 20% pentane), but not containing any Q2-1401 silicone gum.

It was generally found that the compositions containing n-pentane had superior cooling properties to those of the alcoholic deodorant in terms of producing a larger initial temperature drop, i.e. larger degree of cooling.

In addition, both the alcoholic deodorant composition and a composition similar to Example 2 containing 10% pentane and silicone gum were tested on a trained panel to assess the sensory properties for each product. For the two formulations, it was found that both formulations achieved similar ratings for the cold feeling on application, degree of stinging, stickiness and freshness feeling. The composition containing pentane scored higher than the alcohol formulation in terms of the dry feeling it produced.

These results demonstrate that in most assessment criteria, in particular those related to "freshness" on application, compositions according to the invention exhibited similar levels of freshness to a conventional alcoholic deodorant, which in turn would be a higher level of freshness than a conventional antiperspirant aerosol composition. In at least one criterion, the antiperspirant aerosol according to the invention actually surpasses the performance of the alcoholic deodorant composition.

Accordingly, the compositions of the invention have the desirable sensory attributes of a an alcoholic deodorant (i.e. cooling and freshness). In addition, a composition such as Example 1 benefits over an alcoholic deodorant by conferring antiperspirancy (greater than 30% sweat reduction) and significantly greater protection from malodour.

I claim:

1. An aerosol antiperspirant composition for topical application to the human skin, comprising an antiperspirant active and a propellant, characterised in that the propellant comprises pentane.

2. An aerosol antiperspirant composition according to claim 1, wherein the pentane is present at a level of 1–50% by weight of the propellant in the composition.

3. An aerosol antiperspirant composition according to claim 2, wherein the pentane is present at a level of 2–40% by weight of the propellant in the composition.

4. An aerosol antiperspirant composition according to claim 3, wherein the pentane is present at a level of 5–25% by weight of the propellant in the composition.

5. A method for imparting skin cooling properties to an aerosol composition which comprises including pentane in said composition.

6. A method in accordance with claim 5, wherein said aerosol composition comprises an antiperspirant active.

7. A composition in accordance with claim 1 containing less than 1% of short chain monohydric alcohols.

8. A composition according to claim 1, which is anhydrous.

* * * * *